US009962252B2

(12) United States Patent
Eidenschink et al.

(10) Patent No.: US 9,962,252 B2
(45) Date of Patent: *May 8, 2018

(54) AORTIC GREAT VESSEL PROTECTION

(71) Applicant: St. Jude Medical, Cardiology Division, Inc., St. Paul, MN (US)

(72) Inventors: Tracee Eidenschink, Wayzata, MN (US); Matthew Charles Heidner, Maple Grove, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 36 days.

This patent is subject to a terminal disclaimer.

(21) Appl. No.: 14/827,662

(22) Filed: Aug. 17, 2015

(65) Prior Publication Data
US 2015/0351895 A1 Dec. 10, 2015

Related U.S. Application Data

(62) Division of application No. 13/753,015, filed on Jan. 29, 2013, now Pat. No. 9,186,238.

(51) Int. Cl.
*A61M 29/00* (2006.01)
*A61F 2/01* (2006.01)

(52) U.S. Cl.
CPC .............. *A61F 2/01* (2013.01); *A61F 2/013* (2013.01); *A61F 2002/011* (2013.01);
(Continued)

(58) Field of Classification Search
CPC .... A61F 2/01; A61F 2/013; A61F 2230/0093; A61F 2002/016; A61F 2002/011; A61F 2230/0067; A61F 2250/0023
See application file for complete search history.

(56) References Cited

U.S. PATENT DOCUMENTS 3,657,744 A 4/1972 Ersek
4,275,469 A 6/1981 Gabbay
(Continued)

FOREIGN PATENT DOCUMENTS

DE 19857887 A1 7/2000
DE 10121210 A1 11/2002
(Continued)

OTHER PUBLICATIONS

Andersen, H. R. et al, Transluminal implantation of artificial heart valves, European Heart Journal (1992) 13, 704-708.
(Continued)

*Primary Examiner* — Richard Louis
(74) *Attorney, Agent, or Firm* — Lerner, David, Littenberg, Krumholz & Mentlik, LLP

(57) ABSTRACT

A vessel protector system includes an outer sheath, an inner tube disposed within the outer sheath and moveable in a longitudinal direction relative to the outer sheath and at least one protector coupled to the inner tube, each of the at least one protector having a body formed from a filtering material and extending between a leading end and trailing end coupled to the inner tube, the body having a collapsed configuration and an expanded configuration. A snare is coupled to the leading end of the body at one end, and having a second end passing through the interior of the outer sheath, whereby the exertion of a pulling force on the second end of the snare contracts the at least one protector.

15 Claims, 9 Drawing Sheets

(52) U.S. Cl.
CPC . *A61F 2002/016* (2013.01); *A61F 2230/0067* (2013.01); *A61F 2230/0093* (2013.01); *A61F 2250/0023* (2013.01)

(56) References Cited

U.S. PATENT DOCUMENTS

| | | |
|---|---|---|
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,480,423 A | 1/1996 | Ravenscroft et al. |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,685,625 B2 | 2/2004 | Gabbay |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,311,730 B2 | 12/2007 | Gabbay |
| 7,374,573 B2 | 5/2008 | Gabbay |
| 7,381,218 B2 | 6/2008 | Schreck |
| 7,452,371 B2 | 11/2008 | Pavcnik et al. |
| 7,510,572 B2 | 3/2009 | Gabbay |
| 7,524,331 B2 | 4/2009 | Birdsall |
| RE40,816 E | 6/2009 | Taylor et al. |
| 7,585,321 B2 | 9/2009 | Cribier |
| 7,682,390 B2 | 3/2010 | Seguin |
| 7,731,742 B2 | 6/2010 | Schlick et al. |
| 7,803,185 B2 | 9/2010 | Gabbay |
| 7,846,203 B2 | 12/2010 | Cribier |
| 7,846,204 B2 | 12/2010 | Letac et al. |
| 7,914,569 B2 | 3/2011 | Nguyen et al. |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| D660,432 S | 5/2012 | Braido |
| D660,433 S | 5/2012 | Braido et al. |
| D660,967 S | 5/2012 | Braido et al. |
| D684,692 S | 6/2013 | Braido |
| 2002/0004667 A1 | 1/2002 | Adams et al. |
| 2002/0036220 A1 | 3/2002 | Gabbay |
| 2002/0068944 A1 | 6/2002 | White et al. |
| 2002/0068955 A1 | 6/2002 | Khosravi |
| 2002/0095171 A1 | 7/2002 | Belef |
| 2002/0161390 A1 | 10/2002 | Mouw |
| 2002/0161394 A1 | 10/2002 | Macoviak et al. |
| 2003/0023303 A1 | 1/2003 | Palmaz et al. |
| 2003/0050694 A1 | 3/2003 | Yang et al. |
| 2003/0055452 A1 | 3/2003 | Joergensen et al. |
| 2003/0125765 A1 | 7/2003 | Blackledge et al. |
| 2003/0130680 A1* | 7/2003 | Russell .............. A61F 2/01 606/200 |
| 2003/0130726 A1 | 7/2003 | Thorpe et al. |
| 2003/0150821 A1* | 8/2003 | Bates ................. A61F 2/01 210/767 |
| 2003/0176884 A1* | 9/2003 | Berrada ............. A61F 2/013 606/200 |
| 2004/0049262 A1 | 3/2004 | Obermiller et al. |
| 2004/0093075 A1 | 5/2004 | Kuehne |
| 2004/0172056 A1 | 9/2004 | Guterman et al. |
| 2004/0210304 A1 | 10/2004 | Seguin et al. |
| 2005/0096726 A1 | 5/2005 | Sequin et al. |
| 2005/0137695 A1 | 6/2005 | Salahieh et al. |
| 2005/0137697 A1 | 6/2005 | Salahieh et al. |
| 2005/0165441 A1 | 7/2005 | McGuckin et al. |
| 2005/0256566 A1 | 11/2005 | Gabbay |
| 2006/0008497 A1 | 1/2006 | Gabbay |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0173532 A1 | 8/2006 | Flagle et al. |
| 2006/0178740 A1 | 8/2006 | Stacchino et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0112374 A1* | 5/2007 | Paul, Jr. ............. A61F 2/013 606/200 |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2008/0275486 A1 | 11/2008 | Dwyer et al. |
| 2008/0275489 A1 | 11/2008 | Kinst et al. |
| 2009/0069840 A1 | 3/2009 | Hallisey |
| 2009/0112309 A1 | 4/2009 | Jaramillo et al. |
| 2009/0138079 A1 | 5/2009 | Tuval et al. |
| 2009/0270974 A1 | 10/2009 | Berez et al. |
| 2009/0326575 A1* | 12/2009 | Galdonik ........... A61F 2/01 606/200 |
| 2010/0004740 A1 | 1/2010 | Seguin et al. |
| 2010/0036484 A1 | 2/2010 | Hariton et al. |

(56) References Cited

U.S. PATENT DOCUMENTS

| | | |
|---|---|---|
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0185231 A1 | 7/2010 | Lashinski |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0098738 A1 | 4/2011 | Hunt |
| 2012/0130418 A1 | 5/2012 | Jenson et al. |
| 2012/0172915 A1 | 7/2012 | Fifer et al. |
| 2012/0179033 A1 | 7/2012 | Merhi |
| 2012/0179195 A1 | 7/2012 | Lashinski |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| FR | 2847800 A1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 9916382 A2 | 4/1999 |
| WO | 0043062 A1 | 7/2000 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 03047468 A1 | 6/2003 |
| WO | 03077799 A2 | 9/2003 |
| WO | 06073626 A2 | 7/2006 |
| WO | 2006076505 A2 | 7/2006 |
| WO | 07071436 A2 | 6/2007 |
| WO | 08070797 A2 | 6/2008 |
| WO | 10008548 A2 | 1/2010 |
| WO | 10096176 A1 | 8/2010 |
| WO | 10098857 A1 | 9/2010 |

OTHER PUBLICATIONS

Andersen, Henning Rud, Transluminal Catheter Implanted Prosthetic Heart Valves, International Journal of Angiology 7:102-106 (1998).
Design U.S. Appl. No. 29/375,243, filed Sep. 20, 2010.
International Search Report and Written Opinion for Application No. PCT/US2014/012244 dated Oct. 16, 2014.
Knudsen, L.L. et al., Catheter-implanted prosthetic heart valves, The International Journal of Artificial Organs, vol. 16, No. 5 1993, pp. 253-262.
Quaden, René et al., "Percutaneous aortic valve replacement: resection before implantation," 836-840, European J. of Cardio-thoracic Surgery 27 (2005).
Ruiz, Carlos, "Overview of PRE-CE Mark Transcatheter Aortic Valve Technologies", Euro PCR, May 25, 2010.
Transluminal Aortic Valve Placement, Moazami, Nader, et al., ASAIO Journal, 1996; 42:M381-M385.
Zegdi, Rachid, MD, PhD et al., "Is It Reasonable to Treat All Calcified Stenotic Aortic Valves With a Valved Stent?" 579-584, J. of the American College of Cardiology, vol. 51, No. 5, Feb. 5, 2008.

* cited by examiner

AORTIC GREAT VESSEL PROTECTION

CROSS REFERENCE TO RELATED APPLICATIONS

The present application is a divisional of U.S. patent application Ser. No. 13/753,015, filed on Jan. 29, 2013, the disclosure of which is hereby incorporated herein by reference.

BACKGROUND OF THE INVENTION

The present invention is related to protecting against embolism, and more particularly to devices, systems, and methods for the filtration and removal of debris within blood vessels.

A frequent risk in medical procedures is the risk that the procedure will give rise to the formation of potentially life-threatening debris in the patient's bloodstream. Such debris may take the form of plaque or thrombi, which may travel through the patient's vasculature and become lodged in a position that blocks blood flow. For example, during coronary interventions, plaque may become dislodged and/or thrombi may form, both of which could migrate to the carotid arteries, possibly blocking the carotid arteries and causing a stroke.

Moreover, during a heart attack the left atrium can stop beating or go into fibrillation, which will cause temporary stagnation of blood. This blood can coagulate and form clots that can migrate once the heart is returned to normal rhythm. Emergency angioplasty or stent placement may be performed to treat the attack but such procedures typically don't alleviate the problems associated with the coagulated blood.

BRIEF SUMMARY OF THE INVENTION

It has been recognized that the risk of stroke associated with medical procedures can be reduced by using a filter to protect those vessels which are at risk from the procedure.

In view of the need to protect vessels endangered by medical procedures, the present device, system and method were conceived and developed. In accordance with the device, system and method, several examples of vessel protectors are provided.

In some embodiments, a vessel protector system includes an outer sheath, an inner tube disposed within the outer sheath and moveable in a longitudinal direction relative to the outer sheath, at least one protector having a body formed from filtering material and extending between a leading end thereof and a trailing end thereof, the trailing end coupled to the inner tube, the body adapted to be received within the outer sheath thereby having a collapsed configuration and adapted to be discharged from the outer sheath thereby having an expanded configuration, and a snare coupled at one end thereof to the leading end of the body, and having a second end thereof passing through the interior of the outer sheath. The outer sheath may be moveable between a first position receiving the at least one protector and a second position where the at least one protector is discharged therefrom.

In some examples, the filtering material may include at least one of a mesh, a braided material, a shape memory material, and a nickel titanium alloy. The snare may include at least one of a nickel titanium alloy, stainless steel and a polymer thread. The at least one protector may include two protectors, each of the protectors being coupled to an independent snare. The body may form a conical shape in its expanded configuration. The filtering material may include openings of sufficient size to allow the passage of blood but block the passage of particulates greater than a certain size. The openings in the filtering material may be between about 80 um square and about 300 um square. The filtering material may include openings of uniform sizes along the body. The filtering material may include openings of varying sizes such that a section generally midway between the ends of the body has smaller openings than sections bordering the ends of the body.

In some embodiments, a method for protecting blood vessels during a medical procedure includes (i) inserting a vessel protector system into a patient's body, the vessel protector system including an outer sheath, an inner tube disposed within the outer sheath and moveable in a longitudinal direction relative to the outer sheath, at least one protector coupled to the inner tube, each of the at least one protector having a body formed from a filtering material and extending between a leading end and a trailing end which is coupled to the inner tube, the body having a collapsed configuration and an expanded configuration, and a snare coupled to the leading end of the body at one end, and having a second end passing through the interior of the outer sheath, wherein the outer sheath is moveable between a first position covering at least one protector and a second position where the at least one protector is exposed, (ii) positioning the vessel protector system adjacent an open end of at least one blood vessel and (iii) moving the sheath to the second position to deploy the at least one protector, whereby the body of the at least one protector moves to the expanded configuration to filter blood passing through the body into the at least one blood vessel.

In some examples, the method further includes pulling on the snare to contract the body into the collapsed configuration. The method may further include moving the sheath to the first position to cover the at least one protector and removing the vessel protector system from the patient's body.

In some embodiments, a vessel protector system includes an outer sheath, at least one plug having a body formed from filtering material having a collapsed configuration and an expanded configuration, the body in the collapsed configuration adapted to be received within the outer sheath, the body in the expanded configuration being sized and shaped to occupy the cross-section of a blood vessel, and at least one snare having a first end coupled to the body and a second end passing through the outer sheath.

In some examples, the filtering material may be a woven material. The filtering material may be a braided material. The body may be treated with an anti-coagulant. The body may be formed from a shape-memory material. The shape-memory material may be a nickel titanium alloy. The body may have openings that are between about 100 and 1000 microns in their largest dimension when the body is in the expanded configuration. The body may be peanut-shaped or bell-shaped. The at least one plug may include two plugs, the two plugs being coupled in series to the at least one snare. The at least one plug may include two plugs, the two plugs being coupled to different snares.

In some embodiments, a vessel protector system includes an outer sheath, a body of filtering material adapted to be received within the outer sheath thereby having a collapsed configuration and adapted to be discharged from the outer sheath thereby having an expand configuration and at least one snare coupled to the body and extending through the outer sheath.

In some examples, the system may further include an inner tube disposed within the outer sheath and moveable in a longitudinal direction relative to the outer sheath, a trailing end of the body being coupled to the inner tube and the at least one snare passing through the inner tube. The outer sheath may be moveable between a first position receiving the body and a second position where the body is discharged therefrom. The body in the expanded configuration may be sized and shaped to occupy the cross-section of a blood vessel. The body may include a hollow plug.

BRIEF DESCRIPTION OF THE DRAWINGS

Various embodiments of the present system and method will now be discussed with reference to the appended drawings. It is appreciated that these drawings depict only some embodiments and are therefore not to be considered as limiting the scope of the present system and method.

DETAILED DESCRIPTION

In the description that follows, the terms "proximal" and "distal" are to be taken as relative to a user (e.g., a surgeon or an interventional cardiologist) of the disclosed devices and methods. Accordingly, "proximal" is to be understood as relatively close to the user, and "distal" is to be understood as relatively farther away from the user.

Figure 1:
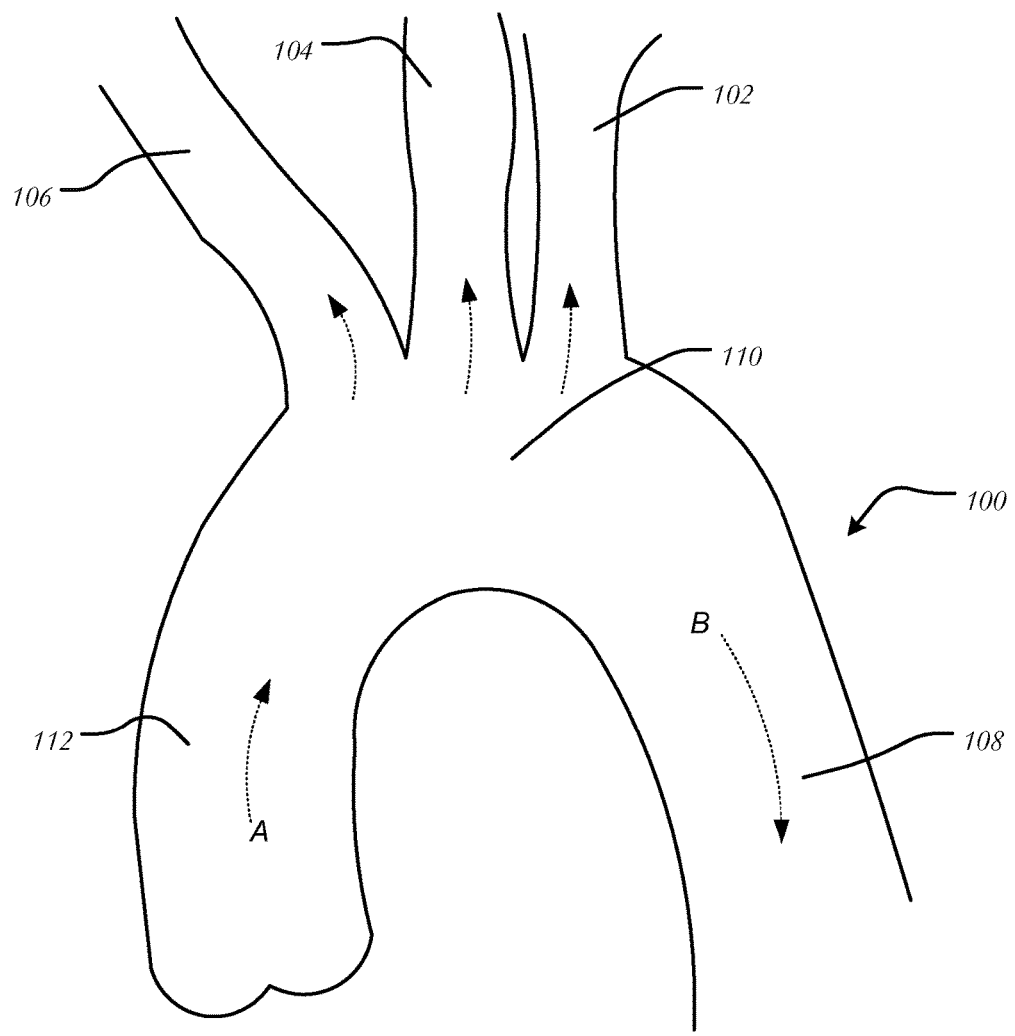
FIG. 1 is a schematic illustration of the aorta.

FIG. 1 illustrates the aorta 100, the largest artery in the body, originating from the left ventricle (not shown) and extending down to the abdomen. Blood flows as indicated by arrow "A" from the left ventricle, through the aortic valve (not shown), through the ascending aorta 112 to the aortic arch 110. Branching from aortic arch 110 are three major arteries: brachiocephalic artery 106, which supplies blood to the right arm and the head and neck, left common carotid artery 104, which supplies blood to the head and neck, and left subclavian artery 102, which supplies blood to the left arm. Blood from ascending aorta 112 not passing through one of these three arteries continues down the descending aorta 108 as shown by arrow "B".

Figure 2A:
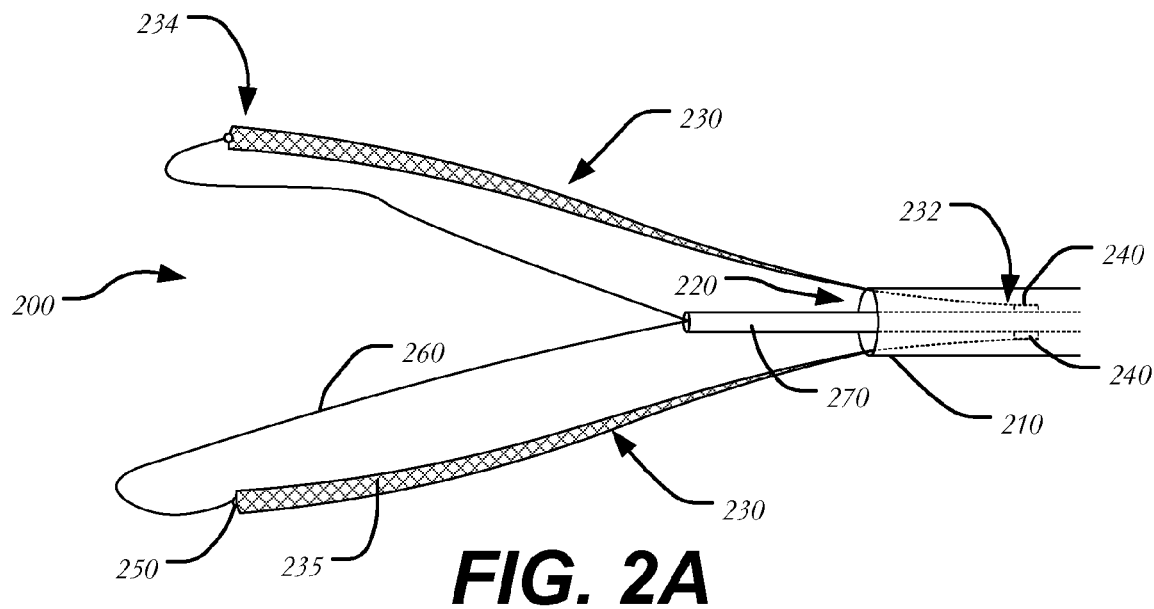
FIG. 2A is a side perspective view of a vessel protector system in accordance with a first embodiment.

Referring to FIG. 2A, there is shown a side perspective view of a vessel protector system 200 in accordance with a first embodiment. As can be seen from FIG. 2A, the vessel protector system 200 includes at least one vessel protector 230, an elongated outer sheath 210, an inner tube 270 disposed within the outer sheath and optionally snare 260.

Sheath 210 and tube 270 are sized to be capable of longitudinal translation with respect to one another. Sheath 210 may be sized according to the vessel in which it will be introduced. For example, when the sheath 210 is to be introduced through the femoral artery, the sheath may be sized in the range of 8 Fr to 12 Fr, depending on the femoral artery diameter.

Junctions 240 are disposed within sheath 210, attached to the outside of inner tube 270. The junctions 240 fixedly attach the trailing ends 232 of the protectors 230 to sheath 210. In some examples, the junctions 240 may be any adhesive, weld or other suitable method of attachment. While FIG. 2A illustrates two protectors 230, it will be understood that vessel protector system 200 may include only a single protector, or three, four or more protectors each having a body as will be described below. Each protector 230 is formed as a sheet-like body 235, which extends between a leading end 234 to the trailing end 232 and serves to filter material entering into any one of the three major arteries that branch off the aortic arch.

Figure 2B:
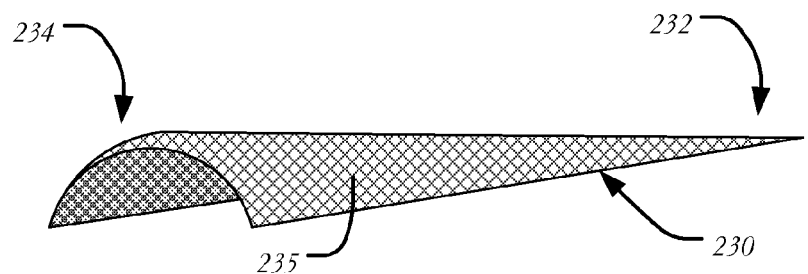
FIG. 2B is an enlarged side perspective view of a protector of the vessel protector system of FIG. 2A.

FIG. 2B is an enlarged side perspective view of a portion of protector 230. As seen in FIG. 2B, the body 235 of protector 230 may be formed from a woven, braided, or knitted material having openings of sufficient size to allow the passage of blood, but block the passage of particulates greater than a certain size. As such, the material of body 235 acts as a filter. The body 235 may have a generally curved shape, such as conical, in use (FIG. 2B), but is collapsible to fit within sheath 210 for delivery into and removal from the patient.

In that regard, body 235 may be formed from a shape-memory material, such as nickel titanium alloy (NiTi, or "nitinol"), that is readily collapsible and that will automatically expand to an operative shape upon deployment from sheath 210. For example, body 235 may be formed from braided nitinol wire, from nitinol wire woven to form a mesh, from a nitinol tube perforated with a plurality of small apertures, and other such structures.

Alternatively, body 235 may be formed from other metals, metal alloys, or polymers such as nylon or polyethylene, that are capable of being woven or otherwise formed into a porous conical shape that may be collapsed and partially disposed within sheath 210 for delivery into and removal from the patient, but that will return to its expanded shape when deployed from the sheath. Still further, body 235 may be formed with a nitinol or other shape-memory frame supporting a fabric layer formed from woven polyester, nylon, polyethylene or similar material. The shape memory frame may cause the fabric layer to achieve the conical shape shown in FIG. 2B upon deployment from sheath 235.

As noted above, the material forming body 235 should have openings of sufficient size to permit the passage of blood, but block the passage of particulates greater than a certain size. In this regard, the openings in body 235 are preferably between about 80 um square and 300 um square. However, these sizes are by way of example only. Body 235 may be self-expanding upon release from sheath 210, or may require the use of one or more instruments to expand following release. A body 235 which is self-expanding may be formed from a biocompatible elastic, superelastic, elastomeric, or shape-memory material which returns to an initial undeformed shape upon release from the sheath 210. Alternatively, a body 235 which is not self-expanding may be formed from a biocompatible material which deforms plastically, and may employ additional snares or other devices such as a frame to effect radial expansion.

In some embodiments, the weave, braid, or knit of the protector body 235 may be varied such that the openings in the mesh vary according to their position on the body. For example, a braided protector body may be formed with a varying opening size such that the section generally midway between the ends of the protector body 235 has smaller mesh openings than the sections bordering the ends of the body. Such a protector body can provide finer filtering at its middle area as compared to its end areas. Other variations in opening size along the length of body 235 are also contemplated herein. Further, the material of protector body 235 may be treated with a conventional anti-coagulant in order to inhibit the coagulation of blood on the body and thus maintain its filtering efficiency.

Referring back to FIG. 2A, the vessel protector system 200 may also include a snare 260 coupled to each of the protectors 230. Snares 260 may be formed of a filamentary material that is attached to the leading end 234 of protector 230 at retraction point 250. The material forming snares 260 should be flexible, yet have sufficient tensile strength to resist breaking when pulled to retract protectors 230. Materials which may be used for snares 260 include conventional suture material, polymeric filaments or thread, thin metal wires such as nitinol or stainless steel, and other such materials.

In one arrangement, a filamentary material forming snare 260 may be connected to retraction point 250 at one end of protector 230 and include a second tail, which extends proximally along the protector, through tube 270, and out from the proximal end of the tube where it may be grasped by a user. When the vessel protector system 200 is being used on a patient, the proximal ends of sheath 210, inner tube 270, and snares 260 may be located outside the patient's body.

Figure 3:
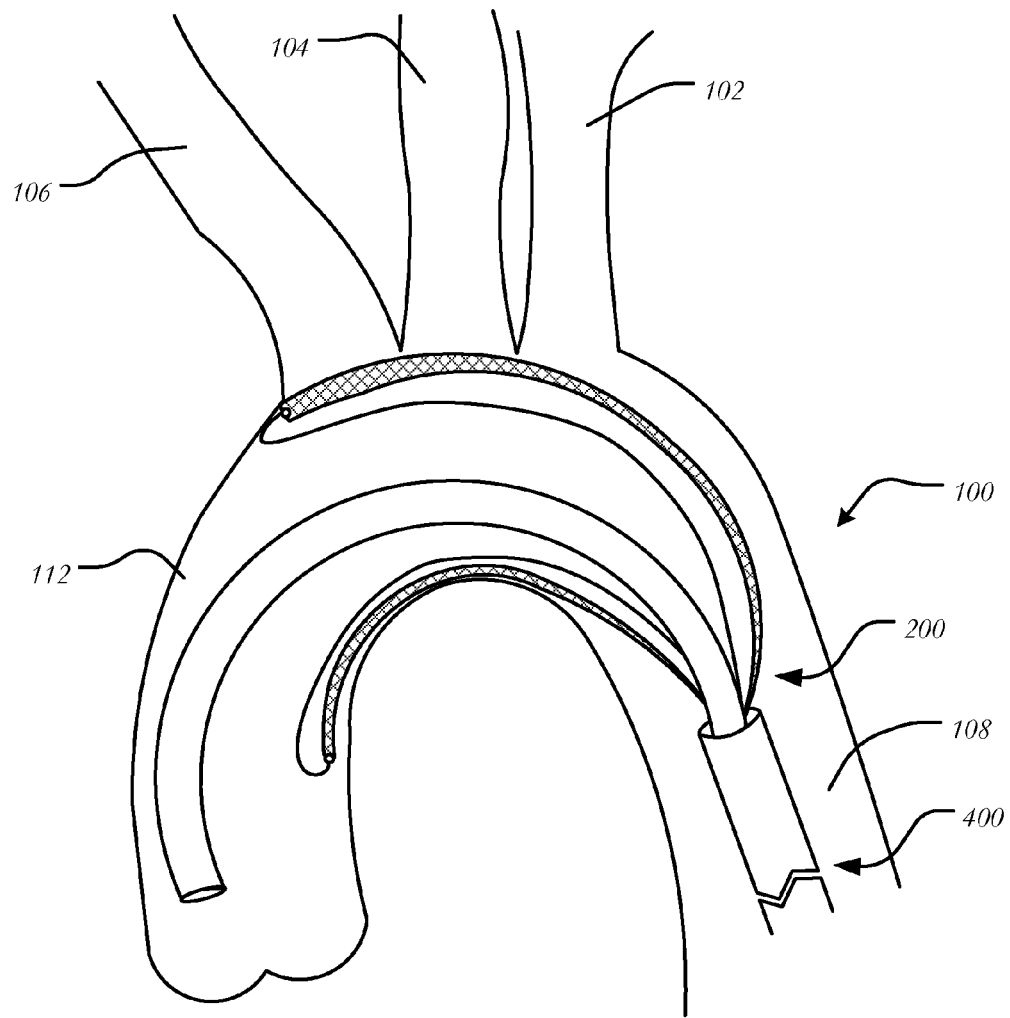
FIG. 3 is a schematic illustration showing the vessel protector system of FIG. 2A in the aorta.

Referring now to FIG. 3, there is shown the vessel protector system 200 of FIG. 2A as used in a coronary intervention procedure, such as for example a transcatheter aortic valve implantation (TAVI) procedure. The figure includes representations of a patient's aorta 10, left subclavian artery 102, left common carotid artery 104 and brachiocephalic artery 106. The vessel protector system 200 has also been introduced to the aorta 100 through, for example, a transfemoral approach.

An operative catheter 400 capable of delivery of a drug or device, or other therapeutic operation has also been introduced to the aorta 100 through a transfemoral approach. As seen in FIG. 3, catheter 400 has been introduced into the aorta through outer sheath 210. It will be understood, however, that catheter 400 may be introduced into the aorta independently of vessel protector system 200. Additionally, the operative catheter and the vessel protector system 200 need not be introduced into the aorta through the same approach. For example, vessel protector system 200 may be introduced transfemorally while operative catheter 400 is introduced transapically or vice versa.

The vessel protector system 200 is introduced to the aorta 100 in a collapsed configuration within sheath 210. Sheath 210 is maneuvered along the aorta 100 until it is in proper position for deployment of protector 230. Once sheath 210 is properly positioned, the user pulls the sheath proximally relative to tube 270 to release the protectors 230. With protectors 230 fully released from the sheath 210 and in proper position, bodies 235 cover the openings to certain arteries as desired while operative catheter 400 performs its intended function. That is, the body 235 expands into a conical shape that acts to filter blood passing through its wall to an artery.

In the scenario described with respect to FIG. 3, the protector 230 is positioned to protect the left subclavian artery 102, left common carotid artery 104 and the brachiocephalic artery 106 from plaque and thrombus that may be released during the cardiovascular procedure. That is, protectors 230 cover the openings of the arteries, with the openings in the filtering material of the body permitting the passage of blood while blocking the passage of plaque and thrombus.

It should be noted that FIG. 3 depicts an illustrative application of protector system 200, and that application of the protector system is not limited to the context of FIG. 3. For example, protector system 200 may be delivered to the patient's aorta 100 through the left radial artery, left brachial artery, or left subclavian artery. Moreover, protector system 200 may be used to protect vessels other than the left common carotid and brachiocephalic arteries, and may be employed in procedures other than coronary intervention. Thus, protector system 200 may be used in any procedure in which there is a possibility that plaque, thrombus or other debris may be introduced into the bloodstream, and in which the protector may be positioned to capture same.

In any event, upon completion of the procedure (e.g., valve implantation) instruments used for the implantation may be withdrawn through sheath 210 or independently and the vessel protector system 200 may be removed from the aorta 100 using the process described below with reference to FIGS. 4A-D.

Figure 4A:
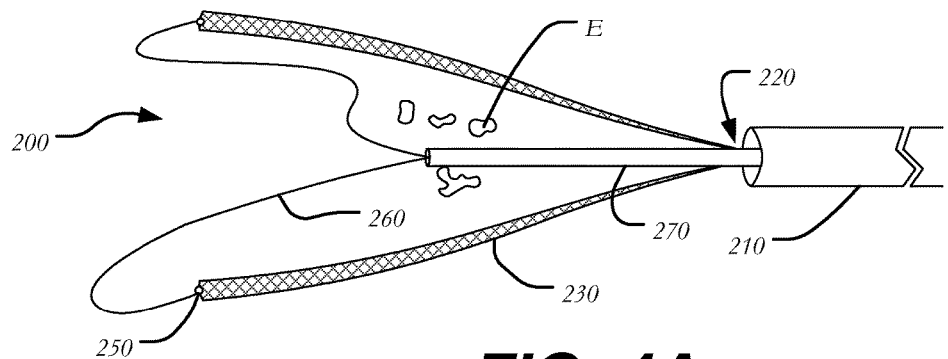
FIGS. 4A-D are schematic illustrations depicting use of the vessel protector of FIG. 2A.

FIG. 4A illustrates the vessel protector system 200 in vivo in its expanded condition. Operative catheter 400 has been removed. Emboli "E", which are any detached, traveling intravascular mass carried by circulation and capable of clogging arterial capillary beds are shown disposed between protectors 230. It would be beneficial to capture and remove emboli "E" so that it does not clog a capillary bed after completion of the operation.

Figure 4B:
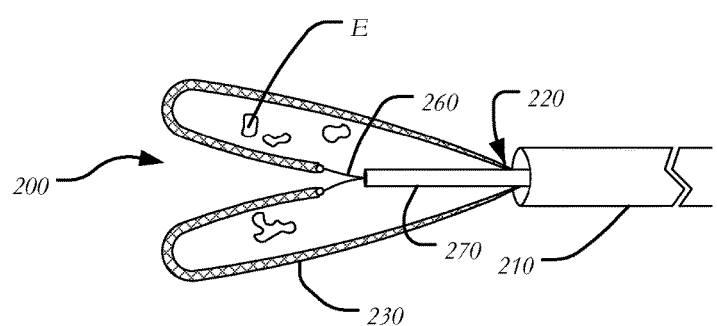
Figure 4C:
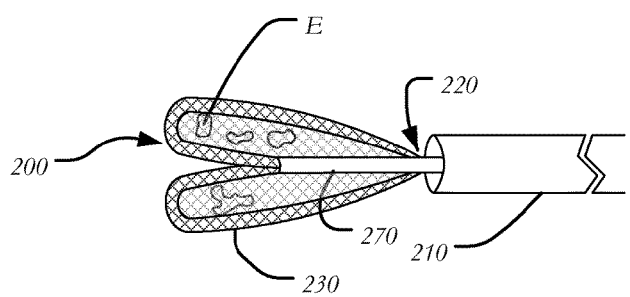

This may be accomplished by grasping the proximal ends of snares 260 and pulling proximally thereon to begin to close protectors 230 while inner tube 270 remains in place. As can be seen in FIG. 4B, the actuation of snares 260 causes the end of the protectors to curve over themselves and pulls the leading end 234 of each protector 230 toward inner tube 270. Emboli "E" are still trapped within protectors 230. Snares 260 may be further pulled through tube 270 until a portion of protectors 230 is disposed within inner tube 270 and emboli "E" is incapable of escaping out of vessel protector system 200 (FIG. 4C).

Figure 4D:
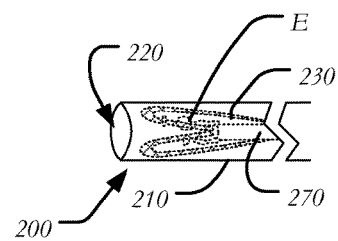

As a final step, sheath 210 may be distally advanced over inner tube 270 and guided over protectors 230 to fully encapsulate tube 270 and protectors 230, which now house emboli "E". FIG. 4D shows the vessel protector system 200 in its fully recaptured state. As can be seen from the figure, protectors 230 are disposed within sheath 210 and emboli "E" has been captured within the vessel protector. Once protectors 230 are fully retracted into sheath 210, vessel protector system 200 may be removed from the patient. Any captured material will be removed from the patient along with protector system 200, and thus will not present a threat of embolism.

Alternatively, emboli "E" may be trapped within protectors 230 and snares may be pulled through tube 270 until protectors 230 seal against sheath 210. Protectors 230 may then be decoupled from tube 270 and the emboli "E" may be aspirated through sheath 210.

In another embodiment, a vessel protector system may include a plurality of permeable blood vessel plugs 310, each blood vessel plug 310 having a body 315 and a stud 350 removably attached to a snare 260. The body 315 of plug 310 may be formed from a woven, braided, or knitted material having openings of sufficient size to allow the passage of blood, but block the passage of particulates greater than a certain size. As such, body 315 acts as a filter. Further, the material of body 315 may be treated with a conventional anti-coagulant in order to inhibit the coagulation of blood on the body and thus maintain its filtering efficiency.

Figure 5A:
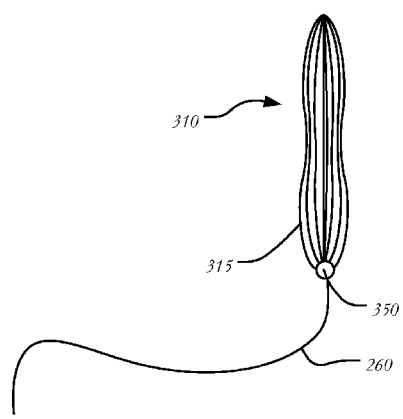
FIG. 5A is a schematic side view of a plug of a vessel protector according to a second embodiment.
Figure 5B:
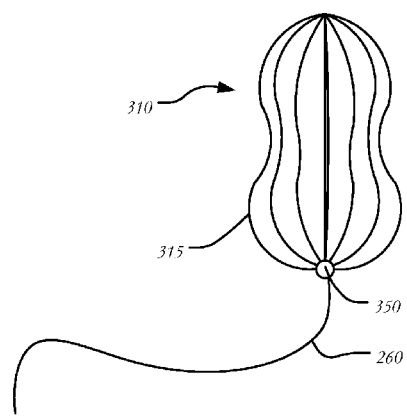
FIG. 5B is a schematic side view of the plug of FIG. 5A in its expanded condition.

FIGS. 5A and 5B illustrate body 315 in its collapsed and expanded conditions. Body 315 is generally hollow, but is collapsible to fit within a sheath (not shown) for delivery and removal from a patient. In that regard, body 315 may be formed from similar materials as protector 230 such as a shape-memory material including, for example, a nickel titanium alloy (NiTi, or "nitinol"), that is readily collapsible and that will automatically expand to an operative shape upon deployment from a sheath, described below. For example body 315 may be formed from braided nitinol wire, from nitinol wire woven to form a mesh, from a simple closed nitinol surface perforated with a plurality of small apertures, or from other such structures.

Alternatively, body 315 may be formed from other metals, metal alloys, or polymers such as nylon or polyethylene, that are capable of being woven or otherwise formed into a hollow shape that is porous and that may be collapsed within a sheath for delivery into and removal from the patient, but which will take on an expanded shape (FIG. 5B) when deployed from the sheath. In some examples, body 315 may have a peanut-shaped expanded condition as seen in FIG. 5B. Still further, body 315 may be formed with a nitinol or other shape-memory frame supporting a fabric layer formed from woven polyester, nylon, polyethylene or similar material. The shape memory frame will cause the fabric layer to achieve an expanded shape upon deployment from the sheath.

In some embodiments, the body 315 of plug 310 may be made up of an outer layer formed from a woven, braided, or knitted material and surrounding a filler material. The filler material could be present to help ensure the capture of embolic debris that fits through the openings in the body's outer layer.

As noted above, the material forming body 315 should have openings of sufficient size to permit the passage of blood, but block the passage of particulates greater than a certain size. In this regard, the openings in body 315 are preferably between about 100 and about 1000 microns in their largest dimension when the body is in the expanded configuration. Thus, for example, when body 315 is made from nitinol braid, the braid spacing is approximately in the range of 100-1000 microns when the body is in the expanded configuration (FIG. 5B).

When body 315 is in the collapsed configuration (FIG. 5A), the openings would be smaller. Further, the size of the openings may vary with the degree to which the body 315 is collapsed. Accordingly, several sizes of plugs may be provided so that a plug 310 is not over-sized or under-sized for the blood vessel in which the plug will be deployed, thereby, avoiding openings that are too small or too large.

Stud 350 may be connected to one end of body 315 and serves as an anchor point for snare 260. In some examples where a set of plugs are connected in series, body 315 may include more than one stud 350, one on each end of body 315 such as described hereinafter. Each stud 350 may be radiopaque so that it may be readily located through, for example, X-ray imaging or fluoroscopy when plug 310 is positioned within a patient. The imaging of stud 350 may help a user place the plug in the proper position and orientation during deployment, and locate the plug for recapture and removal from the patient.

A sheath (not shown in FIGS. 5A and 5B), similar to that described above with reference to the embodiment depicted in FIGS. 2-4, may extend from a distal end sized to hold plug 310 in a collapsed configuration for delivery into and removal from a patient, to a proximal end that remains outside of the patient's body for manipulation by the user. Alternatively, the sheath may have a length that is slightly longer than the length of one or more plugs 310, and may be connected to another shaft member which extends outside of the patient's body so that manipulation of the shaft member by the user will result in a corresponding movement of the sheath. In either event, the sheath/shaft combination may be steerable as is known in the art in order to maneuver the sheath through the patient's vasculature to the desired deployment site.

The snare 260 may be inserted in the proximal end of the sheath, may track through the sheath to be utilized in a blood vessel, and may engage one or more studs 350. That is, snare 260 may be designed to engage either one, or multiple studs 350, but in either case, snare 260 may engage only one of the studs at a given time.

The use of sheath 210 to deliver one or more plugs 310 to a desired location within a patient's aorta will now be described with reference to FIGS. 6-8. To begin, one or more plugs 310 are compressed to a collapsed condition and loaded into sheath 210. The sheath 210 may then be inserted into the patient and maneuvered to the patient's aortic arch using a conventional technique, such as a transfemoral approach, a left subclavian approach, a ventricular apex approach, or other known techniques. In any event, when the distal end of sheath 210 reaches a desired position within the patient's vasculature, the user deploys a plug 310 from sheath 210.

When plug 310 is deployed from sheath 210, body 315 expands into a shape that conforms to the blood vessel within which it is deployed. In this manner, the body 315 fills the entire cross-section of the vessel and no blood can pass through such cross-section without passing through the body. As expanded within a blood vessel, body 315 may be hollow, wadded, or filled with a porous material.

In any case, body 315 has sufficient porosity or openings to permit blood to flow therethrough, but to trap debris. Body 315 is held in place within the blood vessel by an expansive force exerted on the blood vessel by the body material. Accordingly, the material of body 315 must have sufficient radial strength to maintain its position within the blood vessel in the presence of flowing blood. Nevertheless, the radial strength should be low enough to avoid vessel damage in the event that body 315 is dragged along the vessel during positioning or recapture of the plug.

Figure 6:
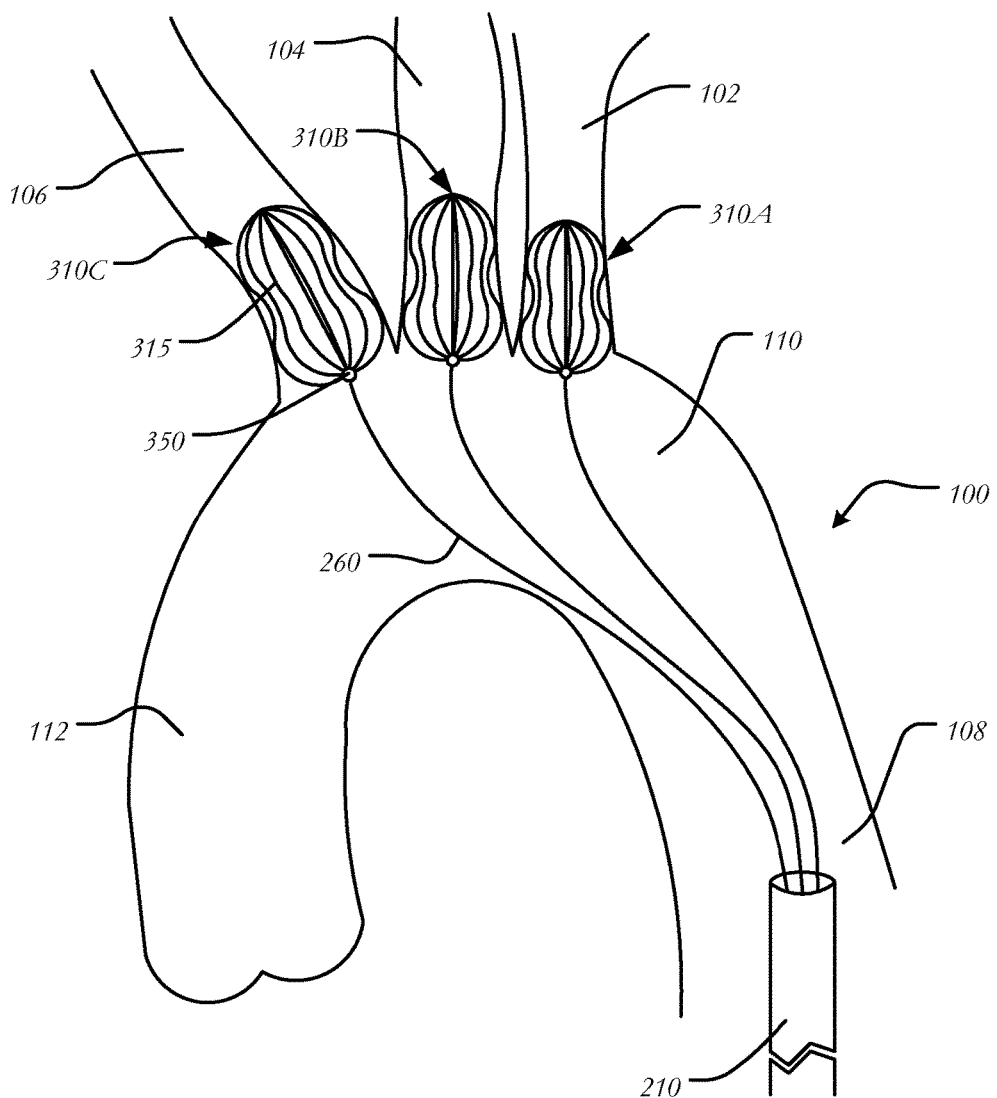
FIG. 6 is a schematic side view of a first method of use of the plug of FIGS. 5A and 5B in the aorta.

FIG. 6 is a schematic view showing the placement of three plugs 310 in a patient's vasculature in preparation for performing a transcatheter aortic valve implantation (TAVI) procedure. The figure includes representations of a patient's aortic arch 110, and a series of plugs 310 to protect the left subclavian artery 102, left common carotid artery 104 and the brachiocephalic artery 106 from plaque and thrombus that may be released during the cardiovascular procedure.

A first plug 310A has been placed in the left subclavian artery 102, a second plug 310B has been placed in the left common carotid artery 104 and a third plug 310C has been placed in the brachiocephalic artery. As shown in FIG. 6, plugs 310A-C have been delivered through a transfemoral approach. However, plugs 310 may be delivered in a retrograde direction from the left subclavian artery, in an antegrade direction from the ventricular apex, or using known alternatives. Several of these alternatives will be described below with reference to FIGS. 7 and 8.

Once plugs 310A-C have been properly deployed, sheath 210 and snare 260 are removed from the patient and the plugs and a medical procedure, such as a TAVI procedure, may be performed. Alternatively, snares 260 may be permanently coupled to plugs 310 and stay within the body until the end of the procedure when they are used to remove the plugs. Since the plug delivery system (sheath 210 and snare 260) has been removed from the patient, the TAVI delivery system may proceed through the patient's vasculature unencumbered by the plug delivery system. In particular, the aortic arch is cleared for passage of the TAVI delivery system. Nonetheless, the permeable plugs 310A-C are in place to filter blood flowing through the aortic arch and into their respective arteries, thereby protecting those arteries and organs downstream thereof against blockage due to debris resulting from the TAVI procedure.

Upon completion of the valve implantation, plugs 310A-C may be removed from the patient. Plugs 310A-C may be removed by reintroducing sheath 210 and snare 260 into the patient, and maneuvering the sheath to a position adjacent one of the plugs. The snare 260 may then be manipulated by the user to grasp one of the studs 350 on the plug. In one example, snare 260 may terminate in a hook to grasp a circular stud 350. Alternatively, studs 350 and snares 260 may be metallic and capable of magnetic attachment. Once the snare 260 has been secured to a stud, the snare may be retracted to draw the associated plug back into sheath 210.

Before drawing plugs 310A-C into sheath 210 for removal from the patient, the plugs may be pulled into the aortic arch 110 to dislodge filtered debris to the peripheral circulation. Optionally, debris may be aspirated from plugs 310A-C by applying a vacuum through sheath 210 or through some other aspiration device, prior to drawing the plugs into the sheath. In any event, as a plug enters the sheath 210, the plug will be compressed to the collapsed configuration, and any debris captured by the plug will be trapped in the sheath.

The plugs may be removed in any order. After the first plug has been retrieved and drawn into sheath 210, the procedure may be repeated to retrieve any additional plugs that had previously been deployed. Where a plurality of plugs have been deployed, the plugs are preferably retrieved in order from the most upstream plug to the most downstream plug to maximize the ability to capture any debris that may be dislodged upon the retrieval of a plug. As seen in FIG. 6, multiple snares 260 may be used in parallel, one coupled to each plug 310.

It should be noted that FIG. 6 depicts an illustrative use of permeable blood vessel plugs 310A-C, and that use of the plugs is not limited to the context of FIG. 6. For example, plugs like those depicted in FIG. 6 may be used in any one blood vessel or combination of blood vessels as desired. The plug used for any particular vessel may be selected from an available set of plugs of various sizes and shapes.

Figure 7:
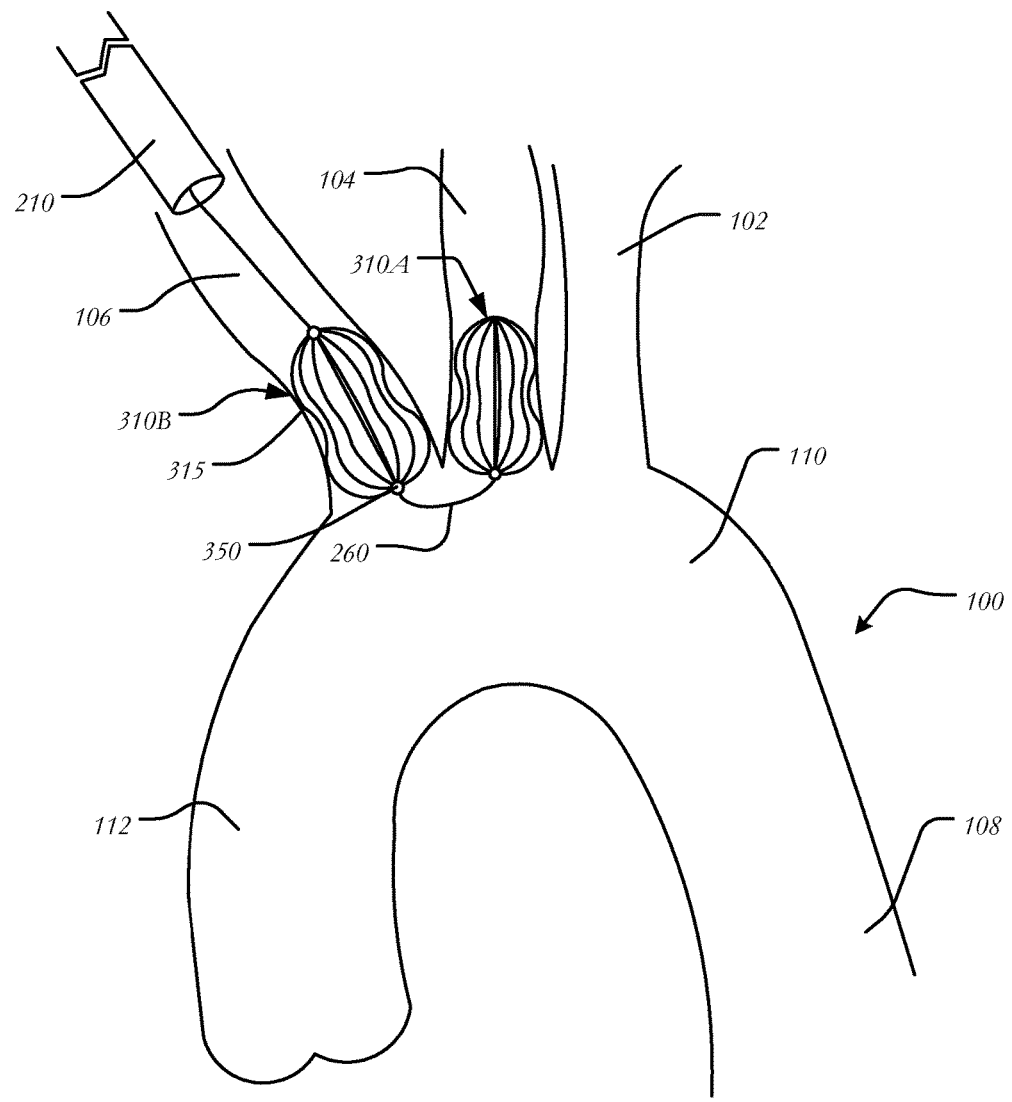
FIG. 7 is a schematic side view of a second method of use of the plug of FIGS. 5A and 5B in the aorta.
Figure 8:
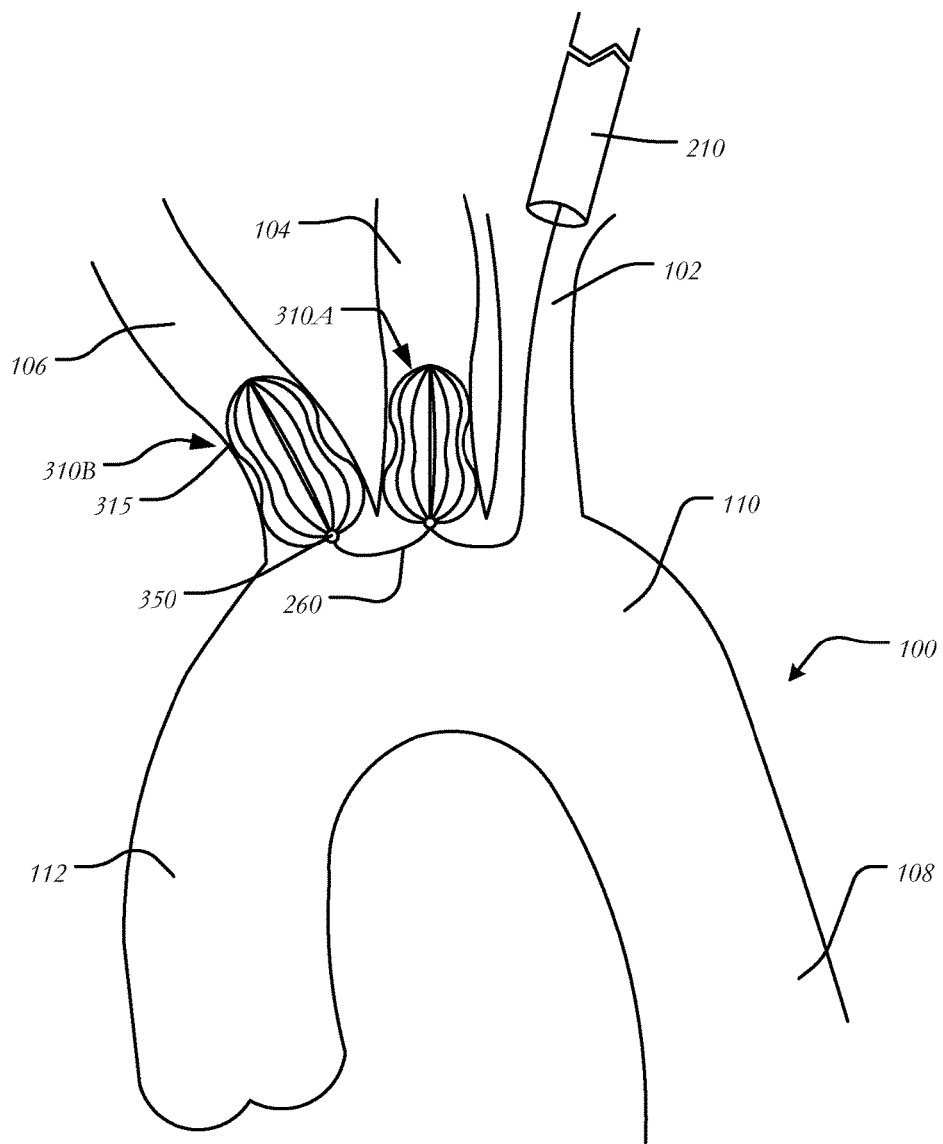
FIG. 8 is a schematic side view of a third method of use of the plug of FIGS. 5A and 5B in the aorta.

FIG. 7 illustrates a sheath 210 being introduced through the brachiocephalic artery. Plugs 310A and 310B are disposed in the left common carotid artery 104 and the brachiocephalic artery, respectively. As seen in FIG. 7, plugs 310A and 310B are arranged in series with a snare 260 connecting plug 310A to plug 310B. In such examples, snares 260 may be permanent, as they do not impede or impinge on the operation of a catheter for therapy or delivery of a drug and/or device. In another alternative, shown in FIG. 8, sheath 210 is introduced through the left subclavian artery and the plugs 310A and 310B are disposed in left common carotid artery 104 and the brachiocephalic artery 106. It will be understood that plugs 310 may be disposed in any combinations of the arteries discussed above. In addition, in certain embodiments, more than one plug may be disposed within an artery.

Figure 9A:
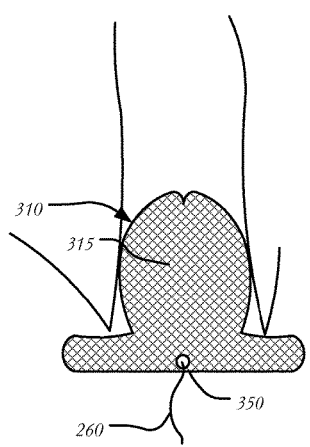
FIGS. 9A-C are schematic illustrations depicting variations of the plugs of a vessel protector.
Figure 9B:
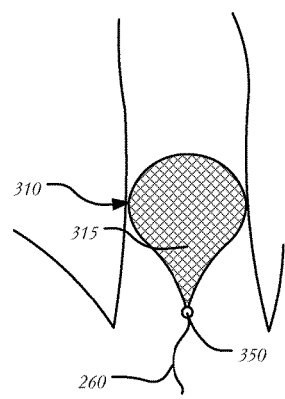
Figure 9C:
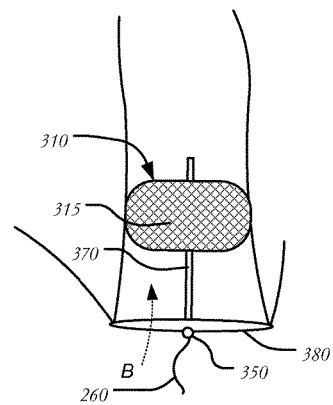

It will be understood that the shapes and sizes of plugs 310 may be varied. FIGS. 9A-C illustrate several alternatives to the peanut-shaped plug of FIGS. 5A and 5B. In a first example (FIG. 9A), a bell-shaped body 315 may be connected to a snare 260 at one end of body 315 via stud 350. It will be understood that stud 350 may be disposed on either side of bell-shaped body 315. A pear-shaped or tear drop-shaped body 315 (FIG. 9B) is shown as a second example, having a stud 350 for coupling to a snare. In a third example, shown in FIG. 9C, a plug 310 includes a body 315 is connected to a disk 380 by way of a rod 370. Body 315 is sized to fit within the vasculature while disk 380 is shaped and/or sized to anchor the body in position and prevent body 315 from traveling in the direction of blood flow "B". Disk 380 may be porous so as to allow to blood to flow through it. Alternatively, disk 380 may include a central aperture to allow blood to flow therethrough.

Although the system and method herein have been described with reference to particular embodiments, it is to be understood that these embodiments are merely illustrative of the principles and applications of the present system and method. It is therefore to be understood that numerous modifications may be made to the illustrative embodiments and that other arrangements may be devised without departing from the spirit and scope of the present system and method as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A vessel protector system, comprising:
   an outer sheath;
   an inner tube disposed within the outer sheath and moveable in a longitudinal direction relative to the outer sheath;
   at least two protectors including a first protector and a second protector, the first and second protectors each having a body formed from filtering material and extending between a leading end and a trailing end, the trailing end being coupled to the inner tube, the body being adapted to be received within the outer sheath in a collapsed configuration and adapted to be discharged from the outer sheath in an expanded configuration; and
   a plurality of snares including a first snare coupled to the first protector and a second snare coupled to the second protector, the first snare being capable of independent actuation relative to the second snare such that actuation of the first snare moves only the first protector and actuation of the second snare moves only the second protector, the first and second snares each extending between a first end and a second end, the second end of the first snare being coupled to and terminating at the leading end of the first protector and the second end of the second snare being coupled to and terminating at the leading end of the second protector.

2. The vessel protector system according to claim 1, wherein the filtering material includes at least one of a mesh, a braided material, a shape memory material, and a nickel titanium alloy.

3. The vessel protector system according to claim 1, wherein each of the plurality of snares includes at least one of a nickel titanium alloy, stainless steel and a polymer thread.

4. The vessel protector system according to claim 1, wherein the at least two protectors comprises exactly two protectors, the two protectors being the first protector and the second protector, the bodies of the first and second protectors each being in the shape of a conical portion having an apex, a base, a first side edge extending from the apex to the base, and a second side edge extending from the apex to the base, the first side edge and the second side edge being spaced apart from one another.

5. The vessel protector system according to claim 1, wherein the at least two protectors comprises exactly two protectors, the two protectors being the first protector and the second protector, the first and second protectors being spaced away from one another.

6. The vessel protector system according to claim 1, wherein the at least two protectors comprises exactly two protectors, the two protectors being the first protector and the second protector, the first and second protectors each having a retraction point at the leading end of the body.

7. The vessel protector according to claim 1, wherein the filtering material includes openings of sufficient size to allow the passage of blood but block the passage of particulates greater than a certain size.

8. The vessel protector according to claim 7, wherein the openings in the filtering material are between about 80 um square and about 300 um square.

9. The vessel protector according to claim 7, wherein the filtering material includes openings of uniform sizes along the body.

10. The vessel protector according to claim 7, wherein the filtering material includes openings of varying sizes along the body.

11. The vessel protector according to claim 7, wherein the filtering material includes openings of varying sizes such that a section generally midway between the ends of the body has smaller openings than sections bordering the ends of the body.

12. A method for protecting blood vessels during a medical procedure, comprising: inserting a vessel protector system into a patient's body, the vessel protector system including an outer sheath, an inner tube disposed within the outer sheath and moveable in a longitudinal direction relative to the outer sheath, a first protector and a second protector, the first and second protectors being discontinuous with one another and each of the at least two protectors having a body formed from filtering material extending between a leading end and a trailing end, the trailing end being coupled to the inner tube, a first snare coupled to the first protector and a second snare coupled to the second protector the first and second snares each extending between a first end and a second end, the second end of the first snare being coupled to and terminating at the leading end of one of the at least two protectors the first protector, the second end of the second snare being coupled to and terminating at the leading end of the second protector: positioning the vessel protector system adjacent an open end of at least one blood vessel; and moving the sheath to the a second position to deploy the first protector, whereby the body of the first protector moves to the an expanded configuration to filter blood passing through the body into the at least one blood vessel.

13. The method according to claim 12, further comprising pulling the first snare to contract the first protector into a collapsed configuration.

14. The method according to claim 13, further comprising deploying the second protector so that the body of the second protector moves to an expanded configuration, and subsequently pulling the second snare to contract the second protector into a collapsed configuration.

15. The method of claim 12, further comprising moving the sheath to a first position to cover the first protector and removing the vessel protector system from the patient's body.

* * * * *